United States Patent [19]

Topham

[11] 4,037,475

[45] July 26, 1977

[54] SAMPLING DEVICE

[75] Inventor: William Henry Topham, Rochester, England

[73] Assignee: The British Petroleum Company Limited, London, England

[21] Appl. No.: 669,637

[22] Filed: Mar. 23, 1976

[30] Foreign Application Priority Data

Apr. 18, 1975 United Kingdom ............... 16067/75

[51] Int. Cl.$^2$ ............................................. G01N 1/14
[52] U.S. Cl. ................................................. 73/422 R
[58] Field of Search ............................. 73/422, 421 B

[56] References Cited

U.S. PATENT DOCUMENTS

| | | | |
|---|---|---|---|
| 3,282,113 | 11/1966 | Sachnik | 73/422 |
| 3,377,867 | 4/1968 | Nitescu | 73/422 |

Primary Examiner—S. Clement Swisher
Attorney, Agent, or Firm—Brooks, Haidt, Haffner & Delahunty

[57] ABSTRACT

A sampling device for insuring a constant rate of sample flow from a conduit regardless of conduit pressure and medium viscosity, particularly in the high pressure and low viscosity ranges. In addition to the constant displacment pump a back pressure valve provides a constant pressure differential across the pump so that "slip" is maintained constant.

5 Claims, 1 Drawing Figure

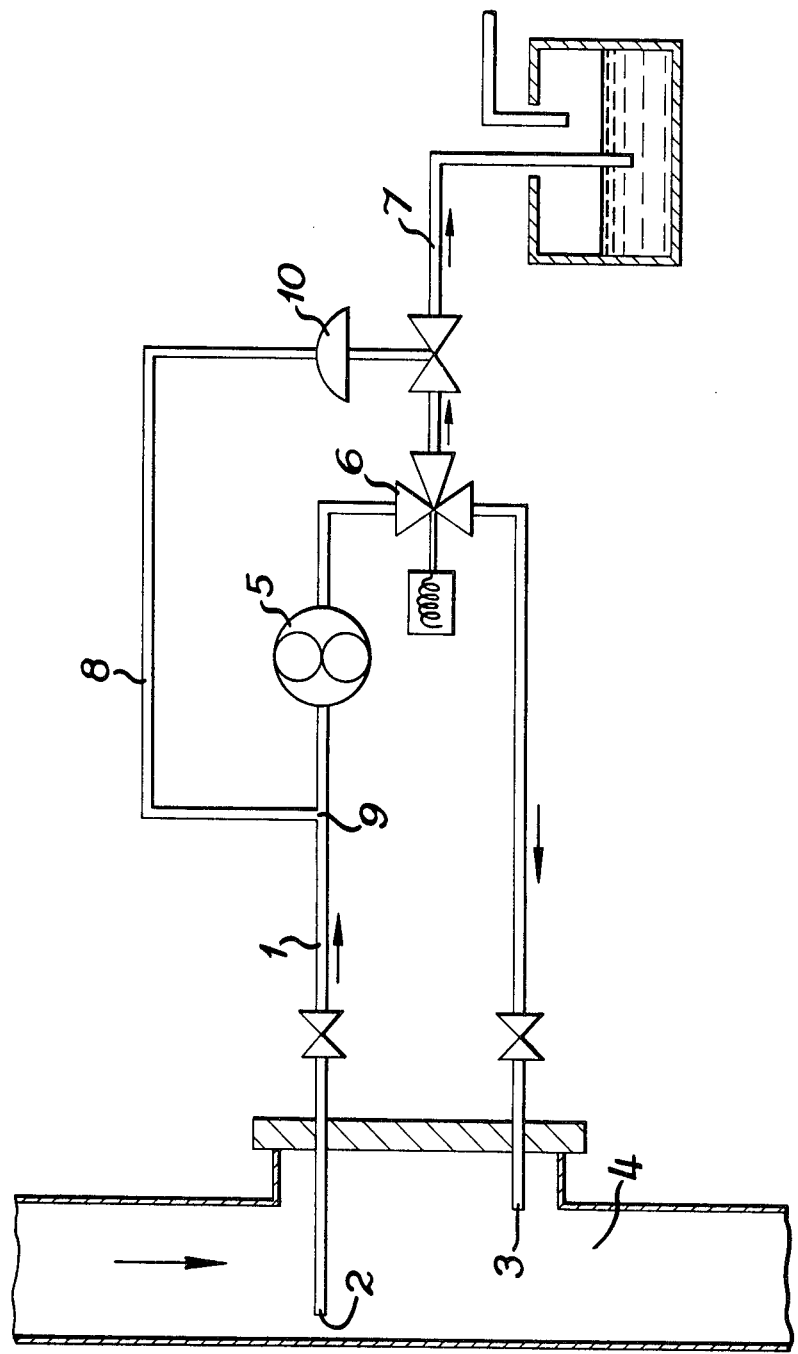

SAMPLING DEVICE

The present invention relates to a device for the elimination of variation in line-pressure and viscosity experienced in automatic devices used for sampling liquids such as crude oil flowing through pipe-lines.

The principal feature of many samplers is the sampling valve, external to the product line, which is opened and closed automatically, e.g. using a solenoid actuated by an electrical signal. The sample may be obtained continuously from the line in either of two ways: It may be done by opening the valve for a fixed period of time to deliver a fixed volume of the liquid to be sampled and, if necessary, varying the frequency of openings depending upon the line flow rate; alternatively, the frequency of the opening may be kept constant but the duration of the opening of the valve may be made proportional to the line flow rate. Whichever technique is used, it is clear that for good results it would be preferable to reduce the effect of line conditions, particularly pressure and liquid viscosity. This may be achieved by incorporating a close tolerance metering pump. Thus, irrespective of the line pressure or viscosity of the liquid being sampled, the pump delivers a representative sample at a constant flow rate. Although this technique may be adequate for medium and high viscosity liquids, on liquids of low viscosity unmetered(slip)flow through clearances in the pump become significant when the sampling is carried out by opening the sample valve.

It has now been found that by incorporating suitable means of pressure control it can be ensured that the sample flow into the receiver when the sampling valve is opened remains constant under all expected conditions of liquid source pressure and liquid viscosity.

Accordingly, the present invention is a liquid sampling device comprising a conduit formed as a loop and having ends which are adapted to be in open communication with a liquid source, a pump capable of circulating liquid at a substantially constant rate through the loop, a sample outlet valve positioned in the loop downstream from the pump and a back-pressure valve adapted to control the flow passage through the sample outlet and responsive to the upstream line pressure to maintain the pressure downstream of the pump during sampling at substantially the same pressure as upstream.

The sampling device of the present invention may be adapted to be used in most process/product stream requiring a representative sample to be taken. The device of the present invention may be used to sample predetermined aliquots of the stream or continuously over a specified time period.

The device is particularly suitable for use on crude oil pipe lines for regular sampling of the oil flowing through such pipe lines.

The conduits and valves of this device may be made of any suitable material depending upon the nature of the liquid being sampled. For example, it may be made from polymeric or metallic material.

The back-pressure valve used in this device may be any of the conventional types actuated by liquid pressure preferably those which would withstand pressures of 400 psig. and upward. The choice would, however, be dictated by the nature of the liquid being pumped and the pressure rating.

The outlet from the sampling valve may be connected to a receiver for the samples. The samples collected in the receivers may thereafter be subjected to any tests as necessary.

The invention is further illustrated with reference to the accompanying drawing.

In the drawing the conduit loop 1 has ends 2 and 3 which are adapted to be in open communication with the crude oil flowing through the pipeline 4. A pump 5 connected to the loop 1 withdraws oil through end 2 and circulates it through the loop 1 via the three-way valve 6 back into the pipe line 4. The three-way valve 6 is provided with a sampling outlet 7, through which a sample may be withdrawn if and when desired. A conduit 8 connects the loop at 9 to a back-pressure valve 10 in the sampling outlet 7. When liquid is pumped through the loop and a sample withdrawn through the sampling outlet 7, the back-pressure valve 10 acts to maintain a constant pressure differential across the pump, thereby ensuring constant flow into the sample receiver. In the absence of the back-pressure valve 10, changes in line pressure or viscosity would cause variations in the flow through the pump leading to inaccuracies in the sampling rate.

I claim:

1. A liquid sampling device comprising a liquid conduit loop including a pair of ends adapted to be in open communication with a liquid source, a pump connected in said loop intermediate said ends for circulating liquid at a substantially constant rate from one of said ends to the other thereof and a sample outlet valve connected in said loop downstream from said pump for removing a sample of liquid from said loop, said valve having an outlet through which said sample flows, and a back-pressure valve connected between said outlet and said loop upstream of said pump, said back-pressure valve being responsive to the liquid pressures at said outlet and in said loop upstream of said pump and maintaining any difference between the pressure at said outlet and the pressure at said loop upstream of said pump substantially constant.

2. A liquid sampling device as set forth in claim 1, wherein the back-pressure valve is capable of withstanding pressures above 400 psig.

3. A liquid sampling device as set forth in claim 2, wherein said ratio is greater than one.

4. A liquid sampling device as set forth in claim 2 further comprising a sample container connected by a fluid conduit to said outlet of said sample outlet valve.

5. A liquid sampling device as set forth in claim 2, wherein said outlet valve is a three-way valve having two settings and which in one said setting thereof permits said liquid to flow from one of said ends to the other thereof and which in the other said setting thereof permits said liquid to flow from said one of said ends through said outlet of said sample outlet valve.

* * * * *

UNITED STATES PATENT AND TRADEMARK OFFICE
CERTIFICATE OF CORRECTION

PATENT NO. : 4,037,475
DATED : July 26, 1977
INVENTOR(S) : William Henry Topham

It is certified that error appears in the above-identified patent and that said Letters Patent are hereby corrected as shown below:

Col. 2, line 49      "claim 2" should read --claim 1--

Col. 2, line 51      "claim 2" should read --claim 1--

Col. 2, line 54      "claim 2" should read --claim 1--

Col. 2, line 55      "said outlet valve" should read --said sample outlet valve--

Signed and Sealed this

First Day of November 1977

[SEAL]

Attest:

RUTH C. MASON
*Attesting Officer*

LUTRELLE F. PARKER
*Acting Commissioner of Patents and Trademarks*